United States Patent [19]

Montague et al.

[11] Patent Number: 5,770,787
[45] Date of Patent: Jun. 23, 1998

[54] NUTRIENT STATUS OF PLANTS IN SOILS

[75] Inventors: James Alexander Montague, Bethanga; Gregory Laurence Bender, New South Wales, both of Australia

[73] Assignee: SGB Australia Pty. Ltd., Melbourne Vic, Australia

[21] Appl. No.: 345,781

[22] Filed: Nov. 22, 1994

[30] Foreign Application Priority Data

Nov. 22, 1993 [AU] Australia ................. PM 2564

[51] Int. Cl.⁶ .............. A01H 5/10; C12N 1/00; A01G 7/00
[52] U.S. Cl. ........... 800/250; 800/200; 435/243; 435/252.1; 435/252.2; 435/256.3; 71/6; 71/31; 71/32; 47/57.6; 47/58
[58] Field of Search ............ 800/200; 435/250, 435/243, 252.1, 256.3, 254.5, 252.2; 504/117; 71/6, 32, 31; 47/57.6, 58, DIG. 9, DIG. 10

[56] References Cited

U.S. PATENT DOCUMENTS 5,026,417  6/1991  Kurey ............................. 71/35

FOREIGN PATENT DOCUMENTS

13149/88  3/1988  Australia .

OTHER PUBLICATIONS

Rupérez et al (1984) Can. J. Microbiol 30: 1157–1162.

Pitt, J.I, In *Advances in Penicillium and Aspergillus Systematics* (Samson and Pitt, eds) 1985, pp. 155–158, Plenum, NY.

*Primary Examiner*—Elizabeth McElwain
*Attorney, Agent, or Firm*—Foley & Lardner

[57] ABSTRACT

A new Penicillium species called *Penicillium radicum* N93/47267 has been isolated. The new *Penicillium radicum* N93/47267 improves the availability of nutrients to plants, particularly in acidic soils. In addition, the new *Penicillium radicum* N93/47267 exercises control over plant fungal pathogens.

13 Claims, No Drawings

NUTRIENT STATUS OF PLANTS IN SOILS

BACKGROUND OF INVENTION

It is well known that phosphorous is an essential nutrient for plants. It is needed for seed formation, root development, strength of straw in cereal crops and crop maturity. Deficiency causes delays in maturity and stunted growth.

Phosphates are often added to soil to counteract a lack of phosphorous. Large deposits of rock phosphates are available in many locations, but untreated rock phosphates have low water solubilities, particularly in neutral or alkaline soils, and consequently do not provide a ready source of phosphorous. In order to overcome this problem, rock phosphates are usually chemically converted to more soluble compounds in large scale fertilizer manufacturing facilities. Commercially available phosphate fertilizers are of many types. More commonly used ones include monoammonium phosphate (MAP), triple super phosphate (TSP), diammonium phosphate, superphosphate and ammonium polyphosphate.

Australian soils are relatively low in total phosphorous but still contain far more phosphorous than is needed by plants. For example, an agricultural soil may contain 600–700 kilograms of phosphorous per hectare to plow depth. A wheat crop yielding 5 tonne of grain per hectare would remove only about 30 kilograms of phosphorous per hectare from this pool. This difficulty is that most of the phosphorous pool is held in insoluble forms which are not available to plants. Hence a farmer must still apply phosphorous as artificial fertilizer for optimum crop yields and to replace phosphorous that is removed from the farm system as produce.

Far more phosphorous is applied as artificial fertilizer than is actually needed by plants because most of the applied phosphorous rapidly becomes unavailable. For example, a wheat crop may use 12% of the current fertilizer phosphorous application. Of the remainder, 71% falls from solution as aluminium, iron or calcium compounds, 4% is immobilized by soil microbes and 13% is incorporated into other soil organic matter. Most agricultural soils, other than sandy soils, can immobilize ore phosphorous than is normally applied as fertilizer. Therefore, a farmer must apply more phosphorous than is taken up by the crop. The overapplication of fertilizer leads to an accumulation of phosphorous in the soil with the soil acting as a "sink" for phosphorous. Consequently, the total phosphorous content of many cultivated soils throughout the world has more than doubled since chemical phosphorous fertilizer usage began in the mid 19th century.

Gaining better access to soil phosphorous reserves and making more efficient use of applied fertilizer phosphorous would reduce fertilizer application rates. Alternatively, making more efficient use of fertilizer phosphorous without reducing current application rates would increase the potential yield of crops. Both courses of action have major benefits for farmers.

INTRODUCTION TO THE INVENTION

Certain microbes have the ability to provide phosphate for plant uptake by solubilization of soil and fertilizer phosphates. The exact mechanism by which microbes solubilize phosphate when in association with plant roots is not known but is thought to be related to their production of organic acids and chelating metabolites.

Canadian scientists have discovered that the presence of soil isolates of the fungus *Penicillium bilaii* in, on or around the roots of wheat and beans results in increased phosphate uptake. These isolates are able to solubilize calcium phosphate and rock phosphate in laboratory studies. A commercial formulation containing a strain of *P. bilaii* for use on wheat to increase the availability of insoluble phosphate for plant uptake has been registered in Canada and is the subject of Australian patent number Au-A-13149/88. The formulation, commercially known as "PB50" or more recently "PROVIDE," is not sold in Australia at present.

Results from field trials in Canada indicate that the product is most suitable for the alkaline soils of Canada but not their acidic soils.

Accordingly, the methods and micro-organism compositions disclosed in AU 13149,88 are not optimally appropriate for the acidic low-phosphate soils which dominate the crop and pasture growing areas of Australia.

The development of a suitable method for improving the availability of phosphorous and other micronutrients from soils characteristic of Australian conditions is clearly desirable to optimize the nutrient potential of Australian soils.

The current invention is a result of a detailed and thorough investigation into the possibility of developing an inoculant product particularly suited to improving the properties of acidic soils and plant growth media.

OBJECT AND STATEMENT OF INVENTION

One object of this invention is to provide a means of improving the properties of plant growth media, including soils, and in particular in respect of the improved availability of phosphorous and other micronutrients from predominantly acidic soils.

Accordingly the invention provides in one aspect a new Penicillium called *Penicillium radicum* (previously called *Penicillium allahabadense*) belonging to the sub-genus *Biverticillium Dierekx* and characterised by the following taxonomic details:

The taxonomic details are based on the regime described by Pitt JI (1979) "The germs Penicillium and its teleomorphic states Eupercillium and Talaromyoes". Academic Press, London.

Czapek Yeast Extract Agar (CYA)
(25° C., 7 days): 10–15 mm diameter; lightly sulcate; velutinous
mycelium: white at the margins but becoming yellow
conidia: greenish grey
exudate: nil
reverse: yellow brown
Malt Extract Agar (MEA)
(25° C., 7 days): 15–20 mm diameter; plane; velutinous to slightly floccose.
mycelium: yellow
conidia: sparse, greenish grey
exudate: nil
reverse: yellow brown
25% Glycerol Nitrate Agar
(25° C., 7 days): germination only or 3–4 mm diameter, plane; velutinous
mycelium: white
conidia: absent
exudate: nil
reverse: buff
CYA at 5° C. no germination
CYA at 37° C.: 10–15 mm diameter, wrinkled colony; velutinous
mycelium: white and yellow
conidia: greenish grey reverse: yellow brown
Conidiophores: borne from surface mycelium
Stipes: length 60–100 $\mu$m
  walls: smooth
Penicilli: bearing terminal biverticillate penicilli (sub-genus Biverticillium)
Metulae: verticils of 4–6; 7–10 $\mu$m long
Phialides: acerose; 7–8 $\mu$m long; long collula
Conidia: subspheroidal to ellipsoidal; 2–3 $\mu$m long; walls smooth to rough; disordered columns.

Penicillium radicum has been deposited with the Australian International Depository Authority (IDA) being the Australian Government Analytical Laboratories of 1 Suakin Street PYMBAL New South Wales 2073 under accession number N93/47267 in accordance with the provisions of the Budapest Treaty concerning the Deposition of Patented Micro-organisms. The deposit was made on 23 Nov. 1993.

Accordingly, in a particularly preferred form the invention provides a *Penicillium radicum* identified as International Deposit Number N93/47267.

In another aspect the invention provides a composition for application or addition to plant growth medial, including soils; or plant products, including seeds; wherein the composition is characterised by the presence of *Penicillium radicum* or *Penicillium radicum* N93/47267 as hereinbefore defined, or an inoculum thereof. Preferably the composition also includes a biologically acceptable carrier which may be a soil compatible carrier for the *Penicillium radicum* or *Penicillium radicum* N93/47267 adapted for the intended mode of delivery of the *Penicillium radicum* or *Penicillium radicum* N93/47267.

The term inoculum as used in this document means any form of vegetative cells (mycelium) or spores of the fungus which are capable of propagating on or in soil when the conditions of temperature, moisture, etc. are favourable for fungal growth. The term "soil-compatible" means any material which can be added to the soil without having any adverse effect on plant growth, soil structure, soil drainage etc.

The fungus can be easily propagated on a suitable carbon source such as sterilized moist ground wheat straw amended with glucose or other sugars. Propagation normally takes place for a period of about one week or more before the inoculum is ready for use. The resulting fungal culture including growth medium may be incorporated into soil, most preferably at the root level, but may also be coated onto seeds if desired. Alternatively, a liquid culture of the fungus may be prepared by using a conventional nutrient solution. The liquid culture may then be used as such or dried and the dried product applied to the soil or seeds wither with or without a suitable carrier and/or nutrient source.

Accordingly, the invention provides a composition comprising a *Penicillium radicum* or *Penicillium radicum* N93/47267 in combination with a soil compatible carrier for direct incorporation into soil or application to seeds as a coating. The soil compatible carrier is most preferably a sterilized moist ground wheat straw amended with glucose on which the *Penicillium radicum* or *Penicillium radicum* N93/47267 has been propagated. In anther embodiment the soil compatible carrier is a liquid culture in which the *Penicillium radicum* or *Penicillium radicum* N93/47267 has been propagated.

It has been found that polysaccharides such as starch or celluose are suitable carriers for the fungal spores. These materials make it easy to handle the spores and also act as carbon sources for the spores when they germinate in the soil. The spores can simply be mixed the carrier (eg. a 50:50 by weight mixture of soluble starch and cellulose) and then the spore content can be adjusted by the addition of further carrier.

The inoculum may consist of a spore/carrier mixture and can be added to a seed row of the soil at the root level or can be used to coat seeds prior to planting. When used to coat seeds the inoculant can simply be mixed with water, applied to the seeds and allowed to dry. Other carriers for the spores can be used to coat seeds.

For example, the spores can be grown on moistened pollard, dried, sieved and applied to seeds prior coated with an adhesive, for example, gum arabic or methylcellulose.

Accordingly, in another aspect the invention provides a plant seed having a coating characterised by an inoculum of *Penicillium radicum* or *Penicillium radicum* N93/47267. The coating of *Penicillium radicum* or *Penicillium radicum* N93/47267 may be adhered or applied without adhesive.

The amount of inoculum applied to the solid is only limited by practical considerations and cost. Obviously, if insufficient is used, a noticeable effect will not be obtained. On the other hand the use of large amounts will be wasteful because the amounts of phosphorous and/or micronutrients made available in the soil reach a maximum at a certain application rate and further additions beyond this do not give additional benefits. The suitable application rates vary with the type of soil, the type of crop plants, the amounts of the type of phosphorous and/or micronutrients present in the soil or added etc. A suitable rate can be found without difficulty by simple trial and experiment for each particular case. Normally, the application rate falls within the range of 0.001–1.0 kg of fungal spores and mycelium (fresh weight) per hectare, or $10^2$–$10^6$ colony forming units (cfu) per seed when coated seeds are used or a few grams of inoculated carrier containing up to about $9\times10^{10}$ cfu/g per meter of plant row.

According, in another aspect the invention provides a method of improving the availability of micronutrients, including phosphorous for plant uptake from the media in which said plants are growing, including soil; characterised by introducing into the said media, within the environment said plants are growing, an inoculum of *Penicillium radicum* or *Penicillium radicum* N93/47267 as hereinbefore defined.

Preferably the inoculum is introduced into the media by the application of a composition as hereinbefore described, most preferable in the environment of the root level of said plants. In an alternative aspect, the inoculum may be introduced into the media by application to the plants themselves or seeds thereof prior to planting.

Since the fungus has the effect of solubilizing phosphates and micronutrients which may already be present in the soil the fungus may be applied alone to soils which contain native sources of phosphorous and/or micronutrients. Alternatively, the fungus may be applied to soils in conjunction with added sources of phosphate and/or micronutrients. Untreated rock phosphate is not only a source of phosphorous, but also usually contains micronutrients such as copper, iron and zinc. Accordingly, the use of *Penicillium radicum* or *Penicillium radicum* N93/47267 in conjunction with added or native rock phosphate forms a preferred aspect of the invention with both phosphorous and micronutrients being made available for plant uptake. Manufactured fertilizers often contain additional micronutrients so a double benefit is obtained when those fertilizers are used with *Penicillium radicum* or *Penicillium radicum* N93/47267. If the phosphorous source does not contain the micronutrients, sparingly soluble sources of these elements may be added to the soil with the *Penicillium radicum* or *Penicillium radicum* N93/47267.

It has been found that the fungus increases the amount of phosphorous available for uptake from commercial phosphorous fertilizers, thus reducing the amounts of these fertilizers required. Therefore, commercial fertilizers may be added to the soil instead of or as well as natural rock phosphates. When pulverized rock phosphate is used as the source of phosphorous and/or micronutrients, the supported fungus may be mixed with pulverized rock phosphate and the resulting mixture introduced into the soil, preferably at the root level, or alternatively the fungus may be added to the soil separately from the rock phosphate.

When a manufactured fertilizer is used as a phosphorous source, it should not be mixed directly with the inoculum because the concentrated fertilizer may weaken or destroy the fungus inoculum. The inoculum and concentrated fertilizer should also be prevented from coming into direct contact in the soil, for example by providing a soil layer between the fertilizer and the inoculum. Other fertilizers, such as nitrogen sources, or other soil amendments may also be added to the soil at approximately the same time as the supported fungus or at other times, so long as the other materials are not toxic to the fungus.

Accordingly, in another aspect the invention provides an enhanced fertilizer product comprising alternate and discrete packaged layers of fertilizer, soil and an inoculum of *Penicillium radicum* or *Penicillium radicum* N93/47267.

Preferably, a carbon source for fungal growth such as ground straw or bran is applied to the soil in addition to the phosphate and *Penicillium radicum* or *Penicillium radicum* N93/47267. The carbon source is additional to the one forming part of the inoculum. The additional carbon source often increases the uptake of nutrients by plants from the soil, presumably because of increased fungal growth rates. The presence of a small amount of nitrogen introduced in the form of the ammonium ion improves the phosphate-solubilizing activity of *Penicillium radicum* or *Penicillium radicum* N93/47267. For this reason ammonium chloride or another ammonium source is preferably applied to the soil at approximately the same time as, or in admixture with, the supported fungus. The amount of the ammonium source added normally falls within the range of 5–20 Kg of nitrogen per hectare. When a manufactured phosphate fertilizer such as MAP is added to the soil, the ammonium need not be added because it is already a component of the fertilizer.

Legume crops (lupin, pea, chickpea, soybean) and pastures (hucerne, clovers) may be inoculated with live Rhizobium bacteria to provide the plant with nitrogen and replace the need for nitrogenous chemical fertilizers. Rhizobium bacteria are supplied to farmers and other end-users in the form of a concentrated pure culture in a moist peat soil powdered carrier. The powdered inoculant is suspended in water and used to coat seed (slurry inoculation or lime pelleting) or directly injected into the soil along with seed when sowing (spray inoculation).

At present legume growers adopting this method apply Rhizobium inoculant to supply nitrogen and chemical fertilizer to supply phosphorous. Accordingly, another aspect of the invention provides a mixed inoculant consisting of Rhizobium bacteria and *Penicillium radicum* or *Penicillium radicum* N93/47267 either separately or in the same packet for the inoculation of legumes and with instructions for the contemporaneous applications of the two active ingredients, thereby supplying nitrogen as well as increasing the availability of soil phosphorous and/or fertilizer phosphorous.

In addition to the aforementioned aspects of the invention, the *Penicillium radicum* or *Penicillium radicum* N93/47267 have numerous applications in the control of plant disease caused by microbial pathogens and in the associated control of plant growth.

Fungi are presently controlled in plants by applying synthetic inorganic or organic chemical fungicides to the area to be treated. A common application method is as a seed coat, commonly referred to as a seed dressing. Chemical fungicides have a number of disadvantages, namely: they are usually toxic to humans, stock and wildlife; they can have undesirable side effects if they accumulate in the environment; target fungi often acquire resistance on prolonged and repeated exposure to the chemical; both production and safe disposal are costly.

Accordingly, in another aspect the invention provides a biological fungicide characterised by a biologically active agent comprising a *Penicillium radicum* or *Penicillium radicum* N93/47267 in combination with a biologically acceptable carries.

The types of fungal pathogens effectively targeted by *Penicillium radicum* or *Penicillium radicum* N93/47267 include but are not limited to *Gaeumannomyces graminis* var *tritici* and var *avenae*, *Rhizoctonia solani*, *Fusarium axysporium*, *Phytopkthora cinamoni*, *Pleichaeta setosa*, *Plasmodiophora brassicae*, *Verticillium dahliae*, *Pythium ultimum*, *Sclerotium rolfsii* and other species belonging to these genera of fungi.

*Penicillium radicum* or *Penicillium radicum* N93/47267 have the effect of significantly inhibiting the activity of the above pathogens.

Accordingly, the invention provides a method of controlling plant disease comprising the use of *Penicillium radicum* or *Penicillium radicum* N93/47267 as a biological fungicide.

Preferably, the *Penicillium radicum* or *Penicillium radicum* N93/47267 is applied to the host seed as an inoculant.

The seed inoculant may be applied as a dressing in conjunction with known chemical seed dressings including Vincit, Armour or Baytan.

In another aspect, the invention provides a method of controlling plant growth comprising the use of *Penicillium radicum* or *Penicillium radicum* N93/47267 as a biological fungicide.

DETAILED DESCRIPTION OF THE PRESENT INVENTION

Example One

In this pot trial, the effect of the fungus *Penicillium radicum* N93/47267 was assessed on wheat plants growing in acidic non-sterile soil in a glass-house.

A red earth soil was collected from a cultivated paddock near Wagga Wagga, New South Wales. The soil of pH4.6 calcium chloride was air dried and sieved through a 2 mm sieve. The soil contained organic matter and 16.9 milligrams of phosphorous per kilogram of soil. Four kilogram of the soil was added to autoclaved 20 centimeter diameter black polypropylene pots and watered so that the bulk was maintained at field capacity while the bottom one centimeter was drier to prevent leaching of nutrients.

*Penicillium radicum* N93/47267 was grown on autoclaved moistened wheat pollard in darkness at 25° C. for two weeks until the pollard particles were covered with mycelium and spores. Ten grams of the colonized pollard was then mixed thoroughly with 80 ml of a 0.5% methyl cellulose solution for 15 minutes. This spore and mycelium suspension contained $2 \times 10^6$ colony forming units per ml. Non-surface sterilized Dollarbird wheat seeds (*Triticum aestivum* cv. Dollarbird) were immersed in the spore and mycellium suspension, stirred for 5 minutes, removed and dried aseptically overnight. The inoculated seeds carried approximately $2\times10^4$ colony forming units per seed.

Four seeds were planted per pot. Five mililiter of sterile potassium dihydrogen phosphate solution or sterile water was added to each pot so that the rate of soluble phosphorus addition was 0, 5, 10, 15 and 20 kilogram of phosphate per hectare. Nitrogen was added as ammonium chloride to all pots every 3 weeks at a rate of 60 kilogram of nitrogen per hectare. Potassium sulphate was also added to the pots every 3 weeks to deliver 30 kilograms of sulphur per hectare and 73 kilograms of potassium per hectare.

For the first seven weeks the pots were watered slowly and gently from above. The soil was maintained at field capacity, and leaching of nutrients avoided. After seven weeks watering was achieved by filling the saucers (volume 260 ml) with water.

After two weeks of growth the plants were thinned out to two per pot.

There were 10 treatments; 5 rates of phosphate addition with and without *Penicillium radicum* N93/47267. Nine replicates of each treatment were arranged in randomized complete blocks on glass-house tables. The blocks were moved one position in a clockwise direction around the glass-house each week, at which time each block was re-randomized.

At intervals during the pot trial physical measurements of all plants were made in an attempt to determine whether there was any trend or statically significant difference in the growth of inoculated and control plants. At week six the number of tillers and leaves were counted and the 4th leaf area was estimated by triangulation (ie. ½×base×length). At week 10 the number of leaves with base width of over 10 mm was counted. Finally, at growth week 14, the length of grain bearing portion of the heads was measured. The plants were harvested at maturity after 20 weeks and were dried at 60° C. for 7 days, weighted and ground. The seeds were ground and analyzed for protein by Near Infrared Reflectance Spectroscopy (Technicon Infra-analyzer 400). Data was subjected to a two-way analysis of variance (ANDVA test) and least significant differences were calculated by an F-test.

Results of the experiment are presented in tables 1 to 4. Inoculation with *Penicillium radicum* N93/47267 produced a reliable increase in the leaf size of plants at all levels of phosphate addition with the exception of 5 kilograms of added phosphate (Table 1) which showed an increase in the number of larger leaves. Tables 1 and 2 show that prior to harvest, inoculated plants at all phosphate levels had a faster growth rate than uninoculated plants.

Improvements in yield as expressed by seed weight, total dry weight and seed protein were only significant when no soluble phosphorous was added and in seed protein only when 15 kilograms of soluble phosphorous was added (Tables 3 and 4). Treatment with inoculant and no added phosphate resulted in a 26.2% increase in seed weight compared to the uninoculated treatment (statistically significant at P<0.01). This represents an equivalent of almost 10 kilograms of added soluble phosphorous per hectare. Total dry weight was increased by 14.7% and seed protein per pot was increased by 23.3% (significant at P<0.05). There was also a 15.1% increase in seed protein per pot for the 15 kilogram of added phosphate per hectare treatment.

Example Two

Control of Take-all disease in Dollarbird wheat by *Penicillium radicum* N93/47267

The fungal pathogen *Gaeumannomyces graminis* produces a disease known as Take-all in wheat and some other grasses. The disease is widespread in wheat growing area in Australia and overseas and causes significant losses to yield. This pot soil trial demonstrates the ability of *Penicillium radicum* N93/47267, applied as a seed inoculant, to control the infestation of wheat by the Take-all fungus.

*Gaeumannomyces graminis* var *tritici* was grown in sterile moistened oat grain for four weeks, air dried at room temperature for seven days and stored at 4° C. The culture was ground into a powder then mixed into soil at a rate of 1 gram per 100 grams soil. Small pots containing 200 grams of infested soil were sown to a depth of one cm with 10 wheat seeds previously slurry inoculated with *Penicillium radicum* N93/47267. Slurry inoculation consisted of mixing 25 grams of *Penicillium radicum* N93/47267 peat culture ($7.3\times10^7$ cfu/g peat) into 100 ml of water. The slurry was mixed over seed at the rate of 4 ml/100 g seed and allowed to air dry before sowing. There were 3 replicates and pots were randomized in blocks in a growth room with a constant 25° C. and day/night light cycle (16 hours/8 hours). Plants were called down to 5 uniform plants per pot and maintained at field capacity. After 8 weeks plant shoot dry weights were determined and root systems assessed for disease, symptoms.

Results

Results are presented in Table 5. The inoculation of wheat seed with *Penicillium radicum* N93/47267 reduced the incidence of Take-all infestation when sowing into soil where the pathogen was present.

Example 3

Assessment of compatibility between *Penicillium radicum* N93/47267 and commonly used chemical fungidcides It is common practice for seed to be coated with chemical fungicides as seed dressings. In some cases it may be advantageous to use *Penicillium radicum* N93/47267 together with a particular chemical dressing on the same seed. Hence the application of *Penicillium radicum* N93/47267 either as a fungicidal seed dressing or a growth promoting inoculant may require compatibility with chemical seed dressings. The following results were obtained after seed dressing with various fungicides followed by inoculation with *Penicillium radicum* N93/47267. The methods used were designed to simulate as closely as possible the actual methods used by wheat growers in the field.

Wheat seed to be treated was pre-sterilized in an over at 70° C. for 3 days. Seed dressings were applied before *Penicillium radicum* N93/47267 inoculant at the recommended rates. *Penicillium radicum* N93/47267 was applied as a peat culture at the rate of 4 ml/100 g of fungicide-treated seed as described in Example 2. Treated and inoculated seed were arranged on malt extract agar plates and secured using a drop of agar solution cooled to 47° C. Plates were incubated at 25° C. and scored for growth after 3 days. Growth of *Penicillium radicum* N93/47267 on and around treated seed indicated tolerance to the particular fungicide.

Results

Results are presented in Table 6. The chemical dressings flutriafol (trade names "Vincit" and "Armour") and triadimenol (trade name "Baytan") could be recommended as compatible with *Penicillium radicum* N93/47267 when used together on seed.

TABLE 1

Plant measurements taken at growth weeks 6, 10 and 14

|  | Index of leaf size by triangulation at 6 weeks (mm²/pot) | Number of leaves >10 mm wide per pot at 10 weeks | Total length of heads of grain at 14 weeks (mm/pot) |
|---|---|---|---|
| Control, nil P addition | 296.1 | 2.4 | 32 |
| Penicillium radicum N93/47267, nil P addition | 404.7*** | 3.6 | 36 |
| Control + 5 kgP/ha | 492.9 | 3.8 | 36 |
| Penicillium radicum N93/47267 + 5 kgP/ha | 532.8 | 5.2** | 39 |
| Control + 10 kgP/ha | 547.9 | 5.1 | 37 |
| Penicillium radicum N93/47267 + 10 kgP/ha | 666.9*** | 5.9 | 37 |
| Control + 15 kgP/ha | 620.6 | 6.9 | 37 |
| Penicillium radicum N93/47267 + 15 kgP/ha | 755.6*** | 7.4 | 45*** |
| Control + 20 kgP/ha | 632.2 | 7.7 | 40 |
| Penicillium radicum N93/47267 + 20 kgP/ha | 779.9*** | 8.9 | 41 |
| LSD: $P < 0.01$ | 107.1 | 1.9 | 6.4 |
| $P < 0.05$ | 80.6 | 1.4 | 4.6 |

**difference between means of inoculated and non-inoculated pots significant at $P < 0.05$ level
***difference between means of inoculated and non-inoculated pots significant at $P < 0.01$ level

TABLE 2

Summary table of increases in plant measurements before harvest due to Penicillium radicum N93/47267

| Soluble P addition (kgP/ha) | Increase in index of leaf size by triangulation at 6 weeks (%) | Increase in number of leaves >10 mm wide per pot at 10 weeks (%) | Increase in total length of heads of grain at 14 weeks (%) |
|---|---|---|---|
| 0 | 36.7*** | 50.0 | 12.5 |
| 5 | 8.1 | 36.8** | 8.3 |
| 10 | 21.7*** | 15.7 | 0 |
| 15 | 21.8*** | 7.2 | 21.6*** |
| 20 | 23.4*** | 15.6 | 2.5 |

**difference between means of inoculated and non-inoculated pots significant at $P < 0.05$ level
***difference between means of inoculated and non-inoculated pots significant at $P < 0.01$ level

TABLE 3

Yields at harvest time

|  | Yield (seed weight) (g/pot) | Total dry weight (g/pot) | Seed protein (g/pot) |
|---|---|---|---|
| Control, nil P addn | 4.39 | 10.85 | 0.60 |
| Penicillium radicum N93/47267, nil soluble P addn | 5.54*** | 12.44*** | 0.74** |
| Control + 5 kgP/ha | 5.24 | 12.29 | 0.69 |
| Penicillium radicum N93/47267 + 5 kgP/ha | 5.77 | 12.80 | 0.72 |
| Control + 10 kgP/ha | 5.59 | 13.29 | 0.77 |
| Penicillium radicum N93/47267 + 10 kgP/ha | 6.01 | 13.60 | 0.87 |
| Control + 15 kgP/ha | 6.57 | 14.42 | 0.86 |
| Penicillium radicum N93/47267 + 15 kgP/ha | 6.94 | 15.84 | 0.99** |
| Control + 20 kgP/ha | 6.75 | 15.31 | 0.87 |
| Penicillium radicum N93/47267 + 20 kgP/ha | 6.96 | 15.28 | 0.91 |
| LSD: $P < 0.01$ | 1.15 | 1.96 | 0.15 |
| $P < 0.05$ | 0.87 | 1.47 | 0.12 |

**difference between means of inoculated and non-inoculated pots significant at $P < 0.05$ level
***difference between means of inoculated and non-inoculated pots significant at $P < 0.01$ level

TABLE 4

Summary table of yield increases due to Penicillium radicum N93/47267

| Soluble P addition (kgP/ha) | Yield (seed weight) increase (%) | Total dry weight increase (%) | Seed protein per pot increase (%) |
|---|---|---|---|
| 0 | 26.2*** | 14.7** | 23.3** |
| 5 | 10.1 | 4.1 | 4.3 |
| 10 | 7.5 | 2.3 | 13.0 |
| 15 | 5.6 | 9.8 | 15.1** |
| 20 | 3.1 | −0.2 | 4.6 |

**difference between means of inoculated and non-inoculated pots significant at $P < 0.05$ level
***difference between means of inoculated and non-inoculated pots significant at $P < 0.01$ level

TABLE 5

Control of Take-all in Dollarbird wheat by Penicillium radicum N93/47267

| Treatment | Average shoot dry weight (mg/pot) | Average number of diseased roots/plant |
|---|---|---|
| Take-all free soil Penicillium radicum N93/47267 (Not Added) | 375 | 0 |
| Take-all added Penicillium radicum N93/47267 (Not Added) | 13 | 3.4 |
| Take-all added Seed inoculated with Penicillium radicum N93/47267 | 337 | 0.7 |

TABLE 6

Compatibility between Penicillium radicum N93/47267 and fungicidal seed dressings

| Fungicide seed dressing | response of Penicillium radicum N93/47267 |
|---|---|
| no dressing around seed | ++++extensive growth of Penicillium radicum N93/47267 |
| Vitavax 750C | +very poor growth of Penicillium radicum N93/47267 |
| Vitavax 200FF | −no growth |
| Raxil CDS | ++uniform growth but strongly inhibited |
| Baytan | +++slight inhibition |
| Armour FS | +++slight inhibition |
| Vincit FS | +++slight inhibition |

The claims defining the invention are as follows:

We claim:

1. Penicillium radicum deposited with the Australian Government Analytical Laboratories and accorded the accession number N93/472267 and herein referred to as *Penicillium radicum* N93/47267.

2. A composition for application or addition to plant growth media or plant products comprising *Penicillium radicum* in accordance with claim 1 in conjunction with soil compatible carrier.

3. A composition in accordance with claim 2 for topical application to plant seeds as a coating, wherein *Penicillium radicum* is present.

4. A composition according to claim 2 wherein the carrier is a polysaccharide.

5. A plant seed characterised by a full or partial topical coating of an inoculum of *Penicillium radicum* in accordance with claim 1.

6. A method of improving the availability of micro nutrients for plant uptake from the media in which said plants are growing comprising the introduction into said media of an inoculum of *Penicillium radicum* in accordance with claim 1.

7. A method according to claim 6, wherein the introduction of said inoculum is made at the root level of said plants.

8. A method of improving the availability of micro nutrients for plant uptake from the media in which said plants are growing, comprising the application to said plants or seeds thereof an inoculum of *Penicillium radicum* in accordance with claim 1 prior to planting.

9. An enhanced plant fertilizer product comprising a phosphorous containing fertilizer, soil and an inoculum of *Penicillium radicum* in accordance with claim 1, said fertilizer, soil and inoculum are packaged in discrete and separate layers in the above order to prevent the direct contact of said fertilizer and said inoculum.

10. A mixed inoculum comprising *Penicillium radicum* according to claim 1 in conjunction with Rhizobium bacteria.

11. A method of controlling take-all disease, comprising steps of:
applying *Penicillium radicum* as claimed in claim 1 to the growing environment of seeds; and
growing seeds in the environment, wherein said *P. radicum* controls infestations by take-all fungus of plants that grow from the seeds.

12. A method according to claim 11, wherein the *P. radicum* is coated on the seeds before sowing.

13. A method according to claim 11, wherein the seeds are wheat seeds.

* * * * *